United States Patent
Granqvist et al.

(10) Patent No.: US 9,648,108 B2
(45) Date of Patent: May 9, 2017

(54) BLUETOOTH SERVICE DISCOVERY

(71) Applicant: Polar Electro Oy, Kempele (FI)

(72) Inventors: Niclas Granqvist, Magenwil (CH); Hannu Kinnunen, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 0 days.

(21) Appl. No.: 14/440,212

(22) PCT Filed: Nov. 28, 2012

(86) PCT No.: PCT/EP2012/073823
§ 371 (c)(1),
(2) Date: May 1, 2015

(87) PCT Pub. No.: WO2014/082665
PCT Pub. Date: Jun. 5, 2014

(65) Prior Publication Data
US 2015/0296020 A1 Oct. 15, 2015

(51) Int. Cl.
*H04B 7/00* (2006.01)
*H04L 29/08* (2006.01)
(Continued)

(52) U.S. Cl.
CPC .............. *H04L 67/12* (2013.01); *A61B 5/002* (2013.01); *H04L 67/16* (2013.01); *H04W 4/008* (2013.01);
(Continued)

(58) Field of Classification Search
CPC ... H04W 4/008; H04B 1/385; A63B 24/0075; A63B 71/0622
(Continued)

(56) References Cited

U.S. PATENT DOCUMENTS 7,789,800 B1 * 9/2010 Watterson ............ A63B 21/005
482/1
2012/0116548 A1 5/2012 Goree et al.

FOREIGN PATENT DOCUMENTS

EP 1968028 A1 9/2008

OTHER PUBLICATIONS

Anonymous: "Bluetooth Low Energy Wireless Technology Backgrounder", Nordic Semiconductor, XP-002711878, pp. 1-8 (2011).

(Continued)

*Primary Examiner* — Eugene Yun
(74) *Attorney, Agent, or Firm* — Hoffmann & Baron, LLP

(57) ABSTRACT

A method provides a service in a Bluetooth device. The method includes initiating, in a first Bluetooth device connection establishment with a second Bluetooth device; carrying out a service discovery procedure with the second Bluetooth device, during which at least one unique service identifier associated with a personal training data service is exchanged between the first Bluetooth device and the second Bluetooth device, wherein the personal training data service comprises at least one personal training data item processed by the first Bluetooth device and/or the second Bluetooth device during a physical exercise; and after the service discovery procedure, transferring at least one frame with the second Bluetooth device, wherein the frame comprises an information element specifying personal training data and a command information element specifying how to process the personal training data.

21 Claims, 3 Drawing Sheets

(51) Int. Cl.
*H04W 4/00* (2009.01)
*A61B 5/00* (2006.01)
*H04W 72/04* (2009.01)
*H04W 8/00* (2009.01)
*A63B 22/02* (2006.01)
*A63B 22/06* (2006.01)

(52) U.S. Cl.
CPC ........... *H04W 8/005* (2013.01); *H04W 72/04* (2013.01); *A63B 22/02* (2013.01); *A63B 22/0605* (2013.01); *A63B 22/0664* (2013.01); *A63B 2220/12* (2013.01); *A63B 2225/15* (2013.01); *A63B 2225/50* (2013.01); *A63B 2230/06* (2013.01)

(58) Field of Classification Search
USPC ........................................................ 455/41.2
See application file for complete search history.

(56) References Cited

OTHER PUBLICATIONS

International Search Report for corresponding PCT Application No. PCT/EP2012/073823, pp. 1-3 (Nov. 9, 2013).

\* cited by examiner

BLUETOOTH SERVICE DISCOVERY

CROSS-REFERENCE TO RELATED APPLICATION

This application is a National Stage application of International Application No. PCT/EP2012/073823, filed Nov. 28, 2012, which is incorporated by reference herein in its entirety.

BACKGROUND

Field

The invention relates to the field of Bluetooth radio communications and, particularly, service discovery in Bluetooth communications.

Description of the Related Art

A Bluetooth® specification defines a generic attribute profile (GATT) for Bluetooth SMART, and the GATT comprises a service discovery protocol (SDP) which enables an application executed in a Bluetooth device to discover services that are available and to determine characteristics of the available services.

SUMMARY

According to an aspect, there is provided a method for providing a service in a Bluetooth device, the method comprising: initiating, in a first Bluetooth device connection establishment with a second Bluetooth device; carrying out a service discovery procedure with the second Bluetooth device, during which at least one unique service identifier associated with a personal training data service is exchanged between the first Bluetooth device and the second Bluetooth device, wherein the personal training data service comprises at least one personal training data item processed by the first Bluetooth device and/or the second Bluetooth device during a physical exercise; after the service discovery procedure, transferring at least one frame with the second Bluetooth device, wherein the frame comprises an information element specifying personal training data and a command information element specifying how to process the personal training data.

According to an aspect, there is provided an apparatus comprising at least one processor and at least one memory including a computer program code, wherein the at least one memory and the computer program code are configured, with the at least one processor, to cause the apparatus to: initiate a Bluetooth connection establishment with a second Bluetooth device; carry out a service discovery procedure with the second Bluetooth device, during which at least one unique service identifier associated with a personal training data service is exchanged with the second Bluetooth device, wherein the personal training data service comprises at least one personal training data item processed by the apparatus and/or the second Bluetooth device during a physical exercise; after the service discovery procedure, transfer at least one frame with the second Bluetooth device, wherein the frame comprises an information element specifying personal training data and a command information element specifying how to process the personal training data.

In an embodiment, the frame is a request frame specifying a read request command for at least one personal training data item, and wherein the at least one memory and the computer program code are configured, with the at least one processor, to cause the apparatus to transfer a response frame associated with said request frame, wherein the response frame comprises the requested personal training data item.

In an embodiment, the frame is a write request frame specifying a write command for a personal training data item comprised in the request frame, and wherein the at least one memory and the computer program code are configured, with the at least one processor, to cause the apparatus to transfer a response frame associated with the request frame, wherein the response frame is an acknowledgment to indicate that the data writing has been successfully completed.

In an embodiment, the apparatus is configured to repeat said exchange of the request frame and the response frame for each personal training data item.

In an embodiment, the apparatus is configured to operate as a server device and to store the personal training data items in a permanent manner. The apparatus may be a personal training device of a user.

In an embodiment the apparatus is configured to operate as a client device and to store the personal training data items in a temporary manner. The apparatus may be configured to discard the personal training data after disconnecting with the second Bluetooth device. The apparatus of may be a gym training apparatus.

In an embodiment, the apparatus is configured to provide dedicated locations for said information elements in a header of the at least one frame, and wherein a unique combination of values of said information elements specifies that the frame belongs to the personal training data service.

According to an aspect, there is provided a computer program product embodied on a non-transitory distribution medium readable by a computer and comprising program instructions which, when loaded into an apparatus, execute a computer process comprising: initiating, in a first Bluetooth device connection establishment with a second Bluetooth device; carrying out a service discovery procedure with the second Bluetooth device, during which at least one unique service identifier associated with a personal training data service is exchanged between the first Bluetooth device and the second Bluetooth device, wherein the personal training data service comprises at least one personal training data item processed by the first Bluetooth device and/or the second Bluetooth device during a physical exercise; after the service discovery procedure, transferring at least one frame with the second Bluetooth device, wherein the frame comprises an information element specifying personal training data and a command information element specifying how to process the personal training data.

Embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1A:
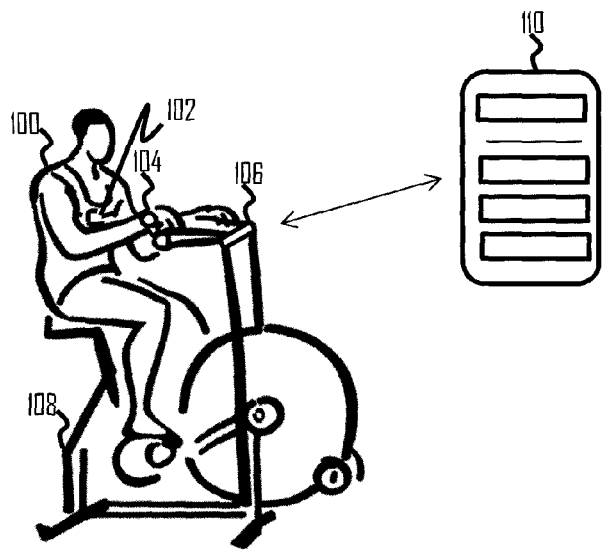
FIGS. 1A and 1B illustrate a personal training scenario to which embodiments of the invention may be applied.

FIG. 1 illustrates a scenario to which embodiments of the invention may be applied. A user 100 is performing a physical exercise on a gym apparatus 108 which is a training bicycle in this example. It should be appreciated that the training bicycle may be replaced by any other gym apparatus or a training apparatus, and other examples comprise a treadmill, a rowing machine, a cross trainer, etc. The gym apparatus 108 comprises a training computer 106 comprising a user interface to display training data to the user 100. The training computer 106 may comprise a wireless communication unit, e.g. a Bluetooth communication circuitry. The training computer 106 may thus be considered to be a Bluetooth device in the context of this description. The user 100 may wear or carry another Bluetooth device or devices which may include a measurement device 102 such as a heart rate transmitter configured to measure the user's 100 heart rate during the exercise or another sensor, a user interface device such as a wrist computer 104 or a palm computer 110 configured to serve as the user's 100 personal training computer storing and processing user's personal profile, training program(s), training data, etc. The palm computer 110 may be a portable computer such as a mobile phone or a tablet computer or, in general, a mobile device.

In another embodiment, the Bluetooth device carried by the user is a tag without UI. The tag may comprise a memory storing data and a communication circuitry enabling an external reader device to read the data from the memory over a wireless connection between the tag and the reader device.

An example of the measurement device 102 is a pedometer, a foot-pod, a shoe-mounted stride sensor, in general a measurement unit 108 attachable to a lower limb of the user. In these examples, the measurement device 102 may comprise a motion sensor in the form of an accelerometer and/or a gyroscope to measure the user's motion during a physical exercise. The measurement device 102 may also comprise a communication circuitry to transmit and receive signals with another device. The communication circuitry may support Bluetooth communications.

Another example of the measurement device 102 is a heart rate monitor configured to measure the users heart rate and possibly other physiological parameters that can be measured from the user. The heart rate monitor may be based on a wireless heart rate monitoring concept where at least one electrode of the heart rate monitor is attached to the user's chest to measure the user's heart rate and to transmit heart rate information telemetrically to a heart rate receiver. The transmission may be based on Bluetooth communication, for example. The heart rate monitor may also be implemented such that the heart rate is directly measured from the wrist on the basis of pressure or optical measurement, for example. In this case, the heart rate monitor may be integrated in the wrist computer 104. Other ways for measuring the heart rate may also be employed.

Other examples of the measurement device include a positioning device configured to determine the user's geographical location on the basis of a satellite navigation system such as the Global Positioning System (GPS).

An embodiment of the invention relates to defining service profiles in a Bluetooth communication protocol, e.g. Bluetooth SMART, and associated service discovery in which bonded Bluetooth devices negotiate about available service profiles. The service profiles may be understood as application level services that are embedded into signalling information of the Bluetooth radio communication protocol. Thus, they may be advertised and discovered by using the signalling that complies with the Bluetooth specifications.

It should be appreciated that the bonding may in some contexts refer to pairing of two Bluetooth devices.

Figure 1B:

FIG. 1B illustrates a server-client concept which may be employed in some embodiments of the invention. A server device 120 provides a client device 122 with a service, and a Bluetooth link 124 may be established between the server device 120 and the client device 122 to provide the service. The Bluetooth signalling may be used to advertise the service by the server device 120 and to carry out service discovery between the server device 120 and the client device 122 in order to explicitly inform the client device 122 about the contents or items of the service(s) provided by the server device 120. With respect to the roles of the client device 122 and the server device 120, the roles may be configured according to the design. If a Bluetooth device is configured to provide at least one service, it may be configured to operate as the server device 120 for said service(s). A Bluetooth device not configured to provide any services is inherently a client device 122. A server device 120 may, however, operate as a slave device for at least one service it does not provide. As a consequence, a Bluetooth device may operate as both the server device 120 and the client device 122. The server device 120 may advertise its service(s), and the client device may scan for advertisements of services, as described below.

Figure 2:
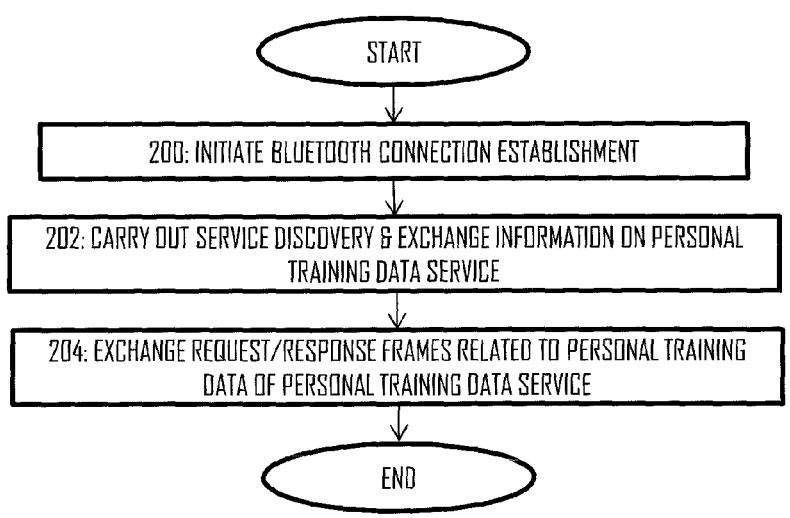
FIG. 2 illustrates a procedure for service discovery in a Bluetooth system according to an embodiment of the invention.

FIG. 2 illustrates a flow diagram of a method for service discovery in a Bluetooth device according to an embodiment of the invention. The Bluetooth device may be advertising a service or services it provides, or it may be detecting the service(s) another Bluetooth device provides. The Bluetooth device may be any one of the above-described Bluetooth devices, e.g. the training computer 106 of the gym apparatus 108, the palm computer 110, the measurement device 102, or the user interface device 104.

Referring to FIG. 2, a first Bluetooth device initiates a connection establishment with a second Bluetooth device in block 200. In block 202, the first Bluetooth device carries out a service discovery procedure with the second Bluetooth device. The service discovery procedure comprises exchange of at least one unique service identifier associated with a personal training data service between the first Bluetooth device and the second Bluetooth device. In an embodiment where the first Bluetooth device provides the service, the exchange may comprise transmission of the at least one unique service identifier from the first Bluetooth device to the second Bluetooth device. In an embodiment where the seconds Bluetooth device provides the service, the exchange may comprise reception of the at least one unique service identifier in the first Bluetooth device from the second Bluetooth device.

After the service discovery procedure, the service may be started, and request frames and response frames may be transferred with the second Bluetooth device in block 204 during the service, wherein a request frame comprises a command information element specifying how to process personal training data specified by the request frame, and wherein a response frame comprises a response to said command of the request frame. Other frames may be transmitted as well and, in general, a frame comprises an information element specifying personal training data and a command information element specifying how to process the personal training data.

This embodiment configures the Bluetooth devices to carry out the service discovery by using control fields of the Bluetooth communication protocol frames. Additionally, the control fields may be used to transfer commands, instructions, and/or notifications as how to process specified personal training data.

The transfer of the frames in connection with the personal training data service may be carried out in the context where the Bluetooth devices transferring the frames have authenticated each other, and encryption may be applied to the transferred data. State of the art Bluetooth device authentication and encryption techniques may be applied.

The first Bluetooth device may be a server device 120 or a client device 122, depending on whether it provides or receives the service. The server device 120 provides the service and the client device 122 receives the service. The server device 120 may store the personal data of the service, and the client device 122 may acquire the personal data from the server device 120 for temporary use, e.g. for the duration of the physical exercise. The client device 122 may rewrite the personal data, e.g. update personal training data stored in the server device 120 with the most recent data acquired during the physical exercise. In the context of the Bluetooth specifications, the server device 120 may be called a generic attribute profile (GATT) server, and the client device 122 may be called a GATT.

Figure 3:
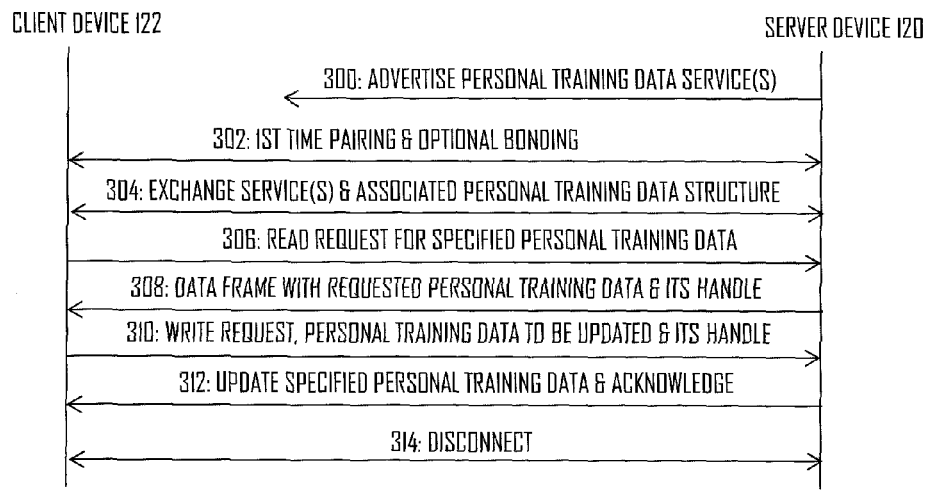
FIG. 3 illustrates a detailed signalling diagram of a procedure for carrying out a personal training data service according to an embodiment of the invention.

FIG. 3 illustrates a signalling diagram of an embodiment for communication between the server device 120 and the client device 122. First, let us consider some embodiments for initial conditions.

In an embodiment, each personal training data service has a universally unique identifier (UUID). Each personal training data service may comprise a database comprising a plurality of training data items. In an embodiment, each personal training data item has a UUID. Each UUID may be a 16-bit, 32-bit, or 128-bit long code word. 16-bit UUIDs are assigned by the Bluetooth SIG and they uniquely identify standardised data within the Bluetooth ecosystem. In addition to the UUID, each training data item may be referred to with a handle. The handle may be understood as a reference or index to a certain record in the database. The handle may be a 16-bit long code word. The use of the UUID and the handle in connection with each personal training data item is described below with reference to FIGS. 3 and 4.

Referring to FIG. 3, the server device 120 may broadcast an advertisement frame in which it advertises the service(s) it provides (300). An advertising interval and timing of the advertising may be selected by bearing in mind connection establishment time and/or power consumption of the server device 120. The advertisement frames may be transmitted on multiple Bluetooth channels, e.g. on three channels. The channels may be distributed in a frequency spectrum available for the server device 120, e.g. one channel may be at a low end of the spectrum, one at a high end of the spectrum, and one in the middle of the spectrum.

The advertisement frame may be a Bluetooth frame comprising an address of the server device 120 and an UUID of each service being advertised. The advertisement frame may comprise an UUID of at least one personal training data service. Table 1 below provides examples of services different server devices may provide.

TABLE 1

| Server device 120 | Service |
|---|---|
| Stride sensor | Speed/cadence service |
| | Device information service |
| | Battery service |
| Heart rate transmitter | Heart rate service |
| | Device information service |
| | Battery service |
| Training computer | Personal data service |
| | Device information service |
| | Training program service |
| Positioning sensor | Location service |
| | Device information service |

The speed/cadence service, heart rate service, and location service may be used to provide training measurement data during a physical exercise and to configure the measurements, a device information service may provide device information on the respective device, a battery service may provide information on battery status of the device. The Bluetooth standard may mandate the Device Information Service to be part of almost all Bluetooth devices.

As described above, each service is associated with an UUID to enable the client devices to explicitly identify each service provided by the server device 120 from the advertisement frame.

In an embodiment, the advertisement frame additionally comprises the UUIDs of the personal training data comprised in each service to enable the client devices to detect what type of data is available for each service. In another embodiment, the UUIDs of the personal training data is provided by the server device 120 in the following service discovery.

Meanwhile, the client device 122 may scan for the advertisement frames transmitted by the server devices in order to detect service advertisements. The client device 122 may scan for potential advertisements continuously at a low duty cycle. The client device 122 may employ a white list comprising as service criteria those services that the client device 122 shall scan for. The white list may be constructed to match with user expectations. For example, a rowing machine may scan for the heart rate service, the user characteristic service, and the training program service but not the speed/cadence service or the location service. A scanning window and a scanning interval may be configured according to user expectations of connection establishment time. A short scanning window and a long scanning interval may cause prolonged connection establishment times.

In an embodiment, the server device 120 may use a Bluetooth's generic access profile (GAP) Undirected Connectable Mode without a white list to allow new client device 122 to establish a connection with the server device 120. In another embodiment, the server device 120 employs the white list such that it allows the connections with only those devices that have been previously bonded with the server device 120, i.e. first-time connections are not allowed.

Upon detecting an advertisement frame comprising a service the client device 122 is scanning for, the client device 122 may be configured to output a notification of a detected service to the user 100 via a user interface of the client device 122. As a use case, let us consider a situation where a user enters the gym and occupies a gym apparatus. Meanwhile, the user's 100 measurement device 102 and/or a training computer 104 may broadcast the advertisement frames detected by the gym apparatus. The gym apparatus may detect the presence of the user by proximity detection and output the list of services it has detected. The proximity detection may be based on a proximity communication between the server device 120 and the client device 122, e.g. a handshake of their near-field communication (NFC) units. The user may then select at least one of the services which triggers bonding between the client device 122 and server device(s) associated with the selected service(s) and the service discovery. Provision of the advertisement enhances the user experience as the server device 120 may be identified by the client device 122 before initiating the connection.

In an embodiment, a name of the server device 120 and/or a name of the owner of the server device 120 (the user's name) is included in the advertisement frames. This enables the client device 122 to greet the user 100 with the user's own name when it detects the presence of the user 100 operating the client device 122. This also enables the user to ensure that the client device 122 has identified the user correctly.

When the bonding has been triggered, either autonomously by the client device 122 or in response to a user input, the client device 122 and the server device 120 may establish a Bluetooth connection between them (302). If the bonding is performed for the first time, the bonding may comprise authentication, negotiation of encryption, and the service discovery, for example. After the first-time bonding, the server device 120 becomes bonded with the client device 122, and the authentication, encryption, and service discovery parameters already negotiated may be assumed in subsequent connection establishments.

The service discovery in step 304 may comprise negotiation of detailed information related to the service(s) provided by the server device 120. The client device 122 may select the service(s) it requests to discover, e.g. those selected by the user, and the discovered services may comprise all the services advertised by the server device 120 or a subset of services advertised by the server device 120. The service discovery of a service may comprise negotiation of the structure of the database associated with the service. The service discovery may comprise negotiation of the UUIDs of the training data items comprised in the service and a handle of each training data item, wherein the handle indicates the location of the training data item in the database of the service. In the service discovery, the client device 122 acquires the handles to be used when addressing each personal training data item in the future.

In an embodiment, the client device 122 filters the discovered training data items. For example, the client device 122 may have a list of training data items it supports, and it may compare the list of training data items comprised in the selected service provided by the server device 120 and select handles of only those training data items it supports. The client device 122 may discard handles of other training data items not supported by the client device 122. In another embodiment, the client device 122 stores the handles of all training data items regardless of whether or not the client device 122 is configured to identify the training data item. In an example of this embodiment, the client device 122 may be configured to process a given training data item even if it cannot identify the contents of the training data item. The client device 122 may then determine as how to process the training data item implicitly from metadata associated with the training data item. For example, the Bluetooth specification allows specification of SI units in connection with a training data item. When the client device 122 detects a training data item having an unsupported UUID but that the training data item is provided in identified SI units, the client device 122 may be configured to display the value of the training data item to the user.

Figure 5:
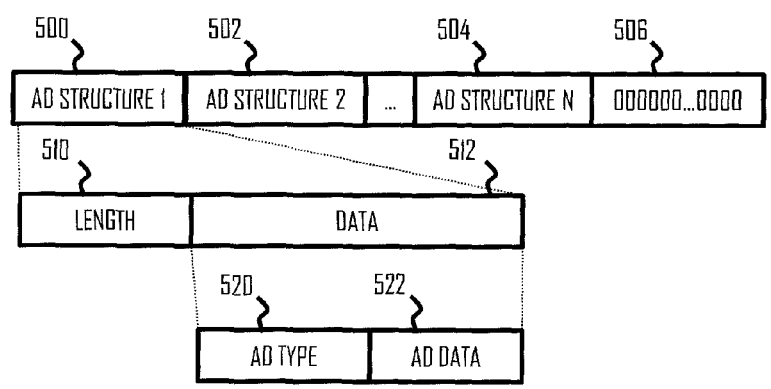
FIG. 5 illustrates a Bluetooth advertising frame comprising information elements according to an embodiment of the invention.

The Bluetooth general access profiles may determine the format of an advertisement frame. The general format of the advertisement frame is illustrated in FIG. 5 as a sequence of advertisement (AD) structures numbered AD Structure 1 500, AD structure 2 502 up till AD structure N 504. Additionally, the frame may comprise an insignificant part 506 comprising arbitrary bits, e.g. zeroes. Each AD structure 500 to 504 may contain a length field 510 indicating the length of the AD structure 500, 502, 504, and an advertisement data field 512 carrying the advertisement data. This frame may be a part of a Bluetooth protocol data unit (PDU) for an advertising channel.

The advertisement data field 512 for the personal training data service may comprise information elements shown in Table 2 below.

TABLE 2

| Length | Advertisement type (AD type) | Advertisement data |
| --- | --- | --- |
| 0x03 | 0x02 | Bluetooth SIG assigned unique ID (UUID) for personal training data service |

The Length field indicates the length of the information element, an AD type field 520 indicates that the advertisement is a Bluetooth service advertisement, and an AD data field 522 comprises a universally unique identifier (UUID) allocated to the personal training data service. The UUID identifies uniquely the personal training data service within the Bluetooth eco system.

As described above, if the service discovery has already been made in connection with a previous connection establishment and the client device 122 has already been bonded with the server device 120, the service discovery may be skipped. When the server device 120 that has been bonded with one or more client device 122 is powered on, e.g. it detects user activity, it may be configured to broadcast the advertisement frames to allow bonded client devices to establish a connection with it. The server device 120 may in this respect use the GAP Undirected Connectable Mode with using a white list to allow bonded devices to initiate the connection. If the connection is not established within a determined period of time, e.g. 10 seconds, the server device 120 may clear the whitelist to allow connection to new, non-bonded client devices.

If the server device 120 is not able to reconnect to one or more client devices within a limited time determined by the implementation, it may continue to advertise periodically.

If the server device 120 is bonded with multiple client devices and a connection is established with a subset of bonded client devices, the server device 120 may continue to advertise periodically to provide the other client devices with an opportunity to initiate a new connection.

The server device 120 may disconnect and enter a low power state, e.g. by switching its radio circuitries off, when it detects no activity from the user within a determined period of time defined by the implementation, e.g. 5 minutes.

Upon establishing the Bluetooth connection between the server device 120 and the client device 122, the devices may exchange frames in relation to the discovered service(s). The frame exchange may follow a request-response principle in which the client device 122 transmits request frames and the server device 120 responds to requests defined in the request frames by transmitting response frames. The request frame may comprise a control field carrying out an information element specifying the nature of the request, and the response frame comprises the same field that indicates the response to the request. Let us now consider read and write requests with reference to FIGS. 3 and 4.

Figure 4:
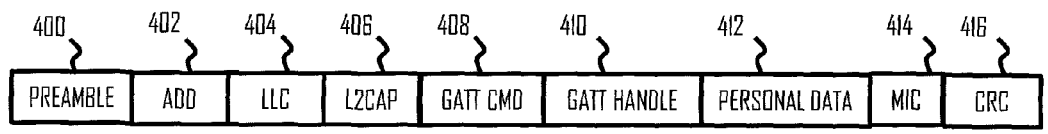
FIG. 4 illustrates a Bluetooth frame format comprising information elements according to an embodiment of the invention.

FIG. 4 illustrates an embodiment of a frame structure used in the requests and responses. The frame comprises a 1-byte preamble 400 used for synchronization, a 4-byte address 402 of a transmitter and/or a receiver of the frame, 2 bytes of link layer control (LLC) information 404, and a logical link control and adaptation protocol (L2CAP) field 406 (2 bytes for length and 2 bytes for a channel identifier) handling (de)multiplexing of data and segmentation and reassembly of data packets, for example. The frame further comprises a GATT field comprising a command (GATT CMD) sub-field 408 and a handle sub-field 410. The command sub-field 408 may specify whether the frame is a request or response frame and/or a read or write frame. The command sub-field 408 may be one byte long, and it may have the following values for different options: a read request=0x0a; a write request=0x12; a read response=0x0b; and a write response=0x13. The handle sub-field 410 (e.g. 2 bytes) may specify the handle of the training data item referred to by the read/write operation. A personal data field 412 may comprise the actual training data item. In connection with some frames, the personal data field may be empty. A message integrity check (MIC) field 414 (4 bytes) may be used in connection with encryption or signing, and a cyclic redundancy check (CRC) field 416 (3 bytes) may be used for error detection and correction.

As mentioned above, the server device 120 stores the personal training data. The server device 120 may be a permanent storage of the personal training data, and the client device 122 may temporarily read the personal training data comprised in the selected service from the server device 120. The reading of the personal training data may be carried out at the beginning of the physical exercise so as to download user characteristics, training program parameters, etc. from the server device 120 to the client device 122, e.g. the gym apparatus. In 306, the client device 122 transmits a read request frame to the server device 120. In the read request frame, the GATT CMD field 408 may be set to correspond to the read request, and the GATT handle 410 may be set to comprise a handle of the requested training data item. The personal data field 412 may be left empty. Upon receiving the read request frame, the server device 120 extracts the contents of the GATT CMD field 408 and the handle 410 and retrieves the training data item stored in the database at the location indicated by the received handle. Thereafter, the server device 120 forms a read response frame comprising the GATT CMD field 408 set to correspond to the read response, the GATT handle 410 set to comprise the handle of the requested training data item, and the contents of the training data item in the personal data field 412. The server device 120 then transmits the read response frame to the client device 122 (step 308). Upon receiving the read response frame, the client device 122 detects from the contents of the transmitter address field 402 and the GATT CMD field 408 that the frame is the read response to the read request frame transmitted by the server device 120, and the client device 122 thus extracts the personal data item from the read response field and stores the personal data item in its database associated with the service and in the location indicated by the handle.

The procedure of steps 306, 308 may be repeated for each personal training data item supported by the client device 122. Each personal training data item may thus be transmitted in a separate read request read response procedure. The personal training data acquired in this manner at the beginning of the physical exercise may comprise the user characteristics such as the age, weight, gender, heart rate limits, and training program data such as the training schedule. Upon acquiring the necessary training data items from the server device 120, the client device 122 is ready for the physical exercise.

The client device 122 may acquire new training data during the exercise. The new training data may comprise performance data, measurement data measured with at least one sensor comprised in the client device 122, and/or data indicating that the training program has been completed according to the schedule. Such new data may be updated to the server device 120. The update may be triggered by the completion of the physical exercise although it should be appreciated that the update may be carried out during the physical exercise. The update of one or more training data items in the server device 120 may be carried out with a write request write response procedure (steps 310, 312). In 310, the client device 122 determines that a training data item should be written into the database of the server device 120 and, as a consequence, it forms a write request frame and transmits it to the server device 120. In the write request frame, the GATT CMD field 408 may be set to correspond to the write request, and the GATT handle 410 may be set to comprise a handle of the training data item to be rewritten. The personal data field 412 may comprise the contents of the training data item to be updated. Upon receiving the write request frame, the server device 120 extracts the contents of the GATT CMD field 408 and the handle 410 and rewrites the training data item indicated by the received handle with the contents of the personal data field 412. Thereafter, the server device 120 forms a write response frame comprising the GATT CMD field 408 set to correspond to the write response, the GATT handle 410 set to comprise the handle of the rewritten training data item, and the personal data field 412 may be left empty. The server device 120 then transmits the write response frame to the client device 122 to acknowledge the completion of the rewriting (block 312). Upon receiving the write response frame, the client device 122 determines that the rewrite has been successful.

The procedure of steps 310, 312 may be repeated for each personal training data item for which the client device 122 has acquired data during the physical exercise. Each personal training data item may thus be rewritten in a separate write request write response procedure.

In step 314, the client device 122 disconnects from the server device 120.

Let us now consider some embodiments of the personal training data items. Table 3 below shows examples of user characteristics and training programs that may be provided as the personal training data items in one or more personal training data services provided by a training computer 104, 110. The personal training data items may be grouped into one or more services, and each personal training data item may belong to multiple services.

TABLE 3

| Personal Data Item Group | Personal Data Item | Data Format | Size |
| --- | --- | --- | --- |
| Constant User Attributes | Name | UTF-8 | 0 . . . 20 Octets |
| | User Identifier | UINT48 | 8 octets |
| | Date of Birth | Opaque structure with year month and day fields | 6 Octets |
| | Gender, unknown, male, female | Enumeration 0-2 | 1 Octet |
| Constant User Attributes/ Contact Details | Street and number | UTF-8 | N Octets |
| | ZiP code | UTF-8 | N Octets |
| | P.O, box | UTF-8 | N Octets |
| | State | UTF-8 | N Octets |
| | Country | UTF-8 | N Octets |
| | Personal Email | UTF-8 | N Octets |
| | Mobile phone | UTF-8 | N Octets |
| | Phone (landline) | UTF-8 | N Octets |
| | Home page | UTF-8 | N Octets |
| Evolving User Attributes | HR Max | UINT8 | 1 Octet |
| | Weight | FLOAT | 4 Octets |
| | Height | UINT16 | 2 Octets |
| | Waist measurement | UNIT16 | 2 Octets |
| | Hip measurement | UNIT16 | 2 Octets |
| User's Physiological Parameters/ training thresholds | Maximum recommended heart rate | UINT8 | 1 Octet |
| | VO2 Max | UINT8 | 1 Octet |
| | Fat burn HR training zone lower limit | UINT8 | 1 Octet |
| | Fat burn HR training zone upper limit | UINT8 | 1 Octet |
| | Aerobic HR training zone lower limit | UINT8 | 1 Octet |
| | Aerobic HR training zone upper limit | UINT8 | 1 Octet |
| | Anaerobic power HR training zone lower limit | UINT8 | 1 Octet |
| | Anaerobic power HR training zone upper limit | UINT8 | 1 Octet |
| | Resting Heart Rate | UINT8 | 1 Octet |
| | Aerobic threshold/ First metabolic | UINT8 | 1 Octet |
| | Anaerobic threshold/ Second metabolic threshold | UINT8 | 1 Octet |
| | Sports types for aerobic and anaerobic Thresholds Sports types enumeration: 0-Unspecified 1Treadmill/running 2-Ergometer/bike 3-Rowing ergometer 4-Arm exercise 5-Elliptical 6-Climber 7-Skiing 8-Skating 9-Lower body 10-Upper body 11-Whole body | Enumeration 0-255 | 1 Octet |
| Training configuration/ program parameters | Number of the players/ runners | UINT24 | 3 Octets |
| | Energy target for next exercise | UINT16 | 2 Octets |
| Accumulated performance/ measurement data | BMR calories per day (historic) | | 2 Octets |
| | Habitual activity calories per day (historic) | | 2 Octets |

TABLE 3-continued

| Personal Data Item Group | Personal Data Item | Data Format | Size |
| --- | --- | --- | --- |
| | Exercise calories per day (historic) | | 2 Octets |
| | Activity volume per week | FLOAT | 4 Octets |
| | Cumulative calories burnt | UINT16 | 2 Octets |
| | Heart rate zones | OPAQUE STRUCTURE with HR values | 5 Octets |
| | 5. Maximum 4. Hard 3. Moderate 2. Light 1. Very Light | UINT16 | |
| Miscellaneous | Database change increment. This number is incremented before any update to the database, e.g. an exercise counter. | UINT32 | 4 Octets |

The personal training data service may be a service additional to other Bluetooth services such as the heart rate service, device Information service and an object transfer service to mention a few.

In an embodiment, at least one frame transferred between the Bluetooth devices as a part of a personal training data service comprises an information element carrying a network address of a network server computer storing the user's user account and user's personal training data. For example, the network server computer may operate as a network storage or a backup storage for the user's server device(s), e.g. the training computer. The network address may be used by the Bluetooth device(s) to access the network server computer and the user account in the network server computer. The user may be authenticated or identified at the network server computer by at least some of the constant user parameters listed above, e.g. the e-mail address, received from the Bluetooth device(s).

Let us now consider some use cases of the personal training data services and associated communication.

User Scenario A—Running on a Treadmill

Stephanie is a motivated runner and loves going to the gym. She trains regularly and likes to measure and analyze her exercises. She recently purchased a fitness application from an online application store for her smartphone, so she can monitor her exercise better. The fitness application may configure the operation of the smartphone as the server device 120, associated personal training data services and the training data items. The configurations of the application may be provided in an extensive markup language (XML). Stephanie usually visits a high tech local gym that has all the latest technology. They are equipped with about 150 different exercise machines to train the whole body and it is a popular gym. They all have Bluetooth and NFC built in. Many of the exercise machines also have streaming audio and she likes to watch music videos while running. It is a pain to setup the stereo headset as it doesn't have NFC. All her training equipment are NFC-enabled and very convenient to use. She starts her exercise program by activating the application on the smartphone which operates as the server device 120. She touches the treadmill with her smartphone (the smartphone with NFC) and, after this proximity detection, they establish a Bluetooth connection.

Optionally, the service discovery is carried out. The treadmill operating as the client device 122 reads Stephanie's personal characteristics, e.g. the name, from the smartphone and greets Stephanie with a welcome message. She now has the option to review and change her personal data. If she changes the personal data, the treadmill may instantly update the personal data to the smartphone by using the write procedure. The review of the personal data may comprise a feature where the treadmill prompts to ensure the most recent weight value is registered within the personal data profile. She may edit the personal data by using the user interface of the treadmill or decline. Using the personal data, the treadmill generates a suitable program for her. Stephanie does her exercise and then finishes. At the end of her session Stephanie presses an 'End session' button on the treadmill's touchscreen. In response to this input, the treadmill may write any measurement data it acquired during the exercise and/or indication that the exercise has been completed to the smartphone by using the write procedure.

In this use case the personal data on the server device 120 may be read and written to, by the client device 122 with minimal or no user intervention as long as they are within communication range. The server device 120 may take no action on its own but wait for the client device 122 to read and write data. The client device 122 may read data in any order. Before writing the data to the server device 120, the client device 122 may request an authorization from the user via the user interface of the client device 122. It may be possible for the user to move from exercise machine to exercise machine and have always up-to-date data on the server device 120. The client device 122 may erase all local data when the connection has ended.

User Scenario B—Multi User Scenario

Nicolas shares his fitness watch/training computer with his wife Cathy. Nicolas goes to a weight training session in the gym on Thursdays and Cathy typically goes to a yoga session on Tuesday. When arriving to the gym, Nicolas starts the session on the training computer. Before starting the exercise session he configures the user of the watch. By changing the user from Cathy to Nicolas, all the machines in the gym will be correctly configured to receive his personal data.

With respect to this use, the server device 120 may comprise multiple user profiles and a database for a personal training data service for each user. The server device 120 may support access to only one person's personal training data items at a time. Accordingly, the server device 120 provides the client device 122 access to training data items of only the currently activated user.

User Scenario C—Synchronising a Heart Rate Sensor and a Training Computer

Stephanie has a heart rate sensor providing the personal training data service. She also has a fitness watch/training computer storing personal data that synchronizes automatically with the heart rate sensor. In the gym, she mostly uses her heart rate sensor only, as the sensor can make bonding automatically at a long distance.

Stephanie connects her heart rate sensor to the training computer and synchronizes their training data items by selecting "synchronize personal data" option. In the gym, Stephanie steps onto a treadmill which, after the connection establishment, identifies the user as Stephanie, greets her welcome, and shows her the personal data Stephanie updates her weight and the data is updated in the heart rate sensor. After the exercise, the treadmill may also update the heart rate sensor with the latest training data acquired by sensors of the treadmill, if any.

The following day Stephanie decides to go for a walk. She takes her training computer and heart rate sensor and starts the exercise. The training computer detects that the data in the heart rate sensor has been updated and asks if Stephanie likes to update the personal data of her training computer or replace the personal data in the sensor. Stephanie decides to update her training computer data by providing a corresponding user input. The detection of an updated training data item in the database may force a rereading of all or a subset of other training data items in the database.

Figure 6:
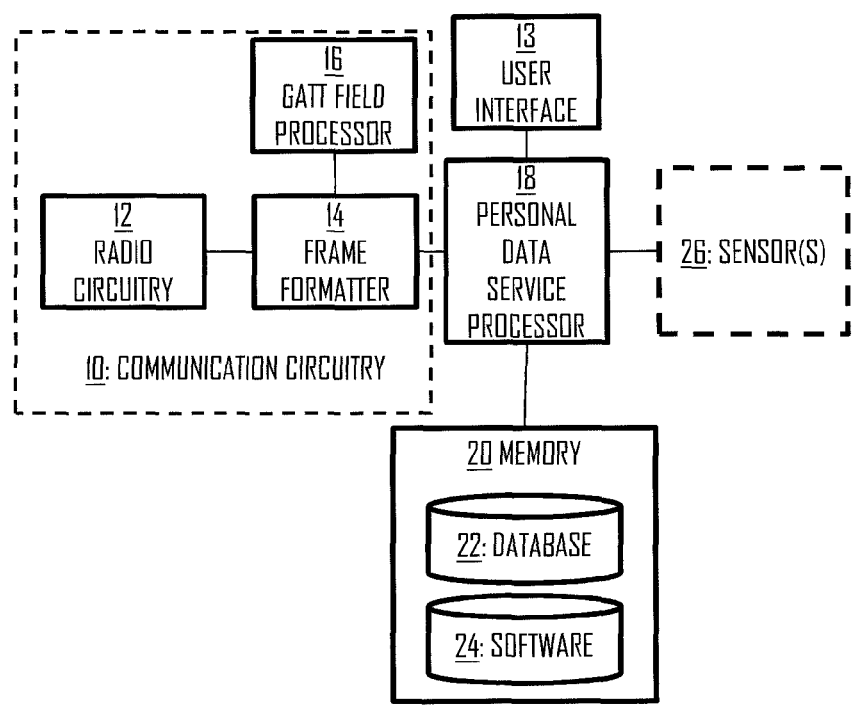
FIG. 6 illustrates a block diagram of an apparatus according to an embodiment of the invention.

FIG. 6 illustrates a block diagram of an apparatus according to an embodiment of the invention. The apparatus may be comprised in a personal training apparatus such as the training computer 110 or the measurement device 102 or in a non-personal training device such as a gym training apparatus. It should be appreciated that the apparatus illustrated in FIG. 5 is a generic illustration encompassing the features of both the client device 122 and the server device 120. The apparatus may be dedicated to operation only as the server device 120 or the client device 122, or it may support both operation modes. One distinguishing feature between the server device 120 and the client device 122 may be that the server device 120 stores the personal training data in a permanent manner, while the client device 122 stores the personal training data in a temporary manner.

Referring to FIG. 6, the apparatus may comprise a personal data service processor 18 operating one or more personal training data services in the apparatus. The personal data service processor 18 may control the execution of the personal training data service(s) on an application level and, optionally, on lower levels. The personal data service processor 18 may have an access to a database 22 stored in a memory 20 of the apparatus and defining personal training data service(s) supported by the apparatus. When the personal data service processor 18 operates in a server mode, the database 22 may also store user profiles and personal training data items associated with each personal training data service. When the personal data service processor 18 operates in a client mode, the database 22 may store personal training data items supported by the personal data service processor per each personal training data service. When the apparatus is operating a personal training data service in the client mode, the database 22 may also store values acquired from the server device 120 for the personal training data items. The personal data service processor may then display at least some of the values to the user via a user interface 13.

When connecting to and communicating with another Bluetooth device, the apparatus may use a communication circuitry 10 configured to form and extract Bluetooth frames in compliance with the Bluetooth specifications. The communication circuitry 10 may comprise a radio circuitry 12 comprising transceiver components needed to transmit and receive radio frequency Bluetooth frames. The communication circuitry 10 may further comprise a frame formatter circuitry 14 configured to form the frame structures and extract received frames. The frame formatter circuitry 14 may comprise or be connected to a GATT field processor 16 configured to process GATT fields of the transmitted/received frames. The GATT field processor 16 may be configured to identify from each received frame whether or not it relates to a personal training data service. With respect to the transmitted frames, it may insert to the frames the GATT command and GATT handle fields 408, 410 that enable a receiver to distinguish that the frame belongs to a personal training data service. The detection that the frame belongs to the personal training data service may be based on a unique value of the handle or a unique combination of the GATT command and the GATT handle fields 408, 410.

The memory 20 may further store one or more computer program products 24 defining a computer progress executed by the personal data service processor and/or the communication circuitry.

The apparatus may further comprise one or more sensor(s) 26 providing measurement data during a physical exercise.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described above in connection with FIGS. 2 to 4 may also be carried out in the form of a computer process defined by a computer program 24. The computer program 24 may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

The present invention is applicable to personal training devices defined above but also to other systems employing the personal training data applications. The protocols used, the specifications of the Bluetooth system develop rapidly. Such development may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

What is claimed is:

1. A method for providing a service in a Bluetooth device, the method comprising:
   initiating, in a first Bluetooth device connection establishment with a second Bluetooth device;
   carrying out a service discovery procedure with the second Bluetooth device, during which the first Bluetooth device informs the second Bluetooth device of a personal training data service and broadcasts a radio frequency discovery frame comprising at least one unique service identifier that uniquely identifies the personal training data service, wherein the personal training data service is provided by the first Bluetooth device and processes at least one personal training data item that represents personal training data associated with a user during a physical exercise; and
   after the service discovery procedure, transferring at least one radio frequency frame from the second Bluetooth device, wherein the radio frequency frame comprises an information element specifying personal training data associated with a user of the discovered personal training data service and a command information element specifying how to process the personal training data specified by the information element associated with the frame.

2. The method of claim 1, further comprising:
   associating each personal training data item with a unique identifier;
   exchanging at least one unique identifier of the personal training data item during the service discovery procedure so as to determine at least one personal training data item associated with the personal training data service; and
   arranging the at least one frame to comprise an information element specifying a personal training data item referred to by the frame.

3. The method of claim 2, further comprising:
   associating each unique identifier of the personal training data item with a handle identifier specifying location of the personal training data item in a database of the personal training data service; and
   providing the handle identifier in each frame to specify the personal training data item referred to by the frame.

4. The method of claim 3, further comprising exchanging a structure of the database during the service discovery procedure by exchanging said handle identifiers of the personal training data items stored in the database.

5. The method of claim 1, further comprising providing a frame comprising no personal training data item or only one personal training data item.

6. The method of claim 1, wherein the frame is a request frame specifying a read request command for at least one personal training data item, the method further comprising transferring a response frame associated with said request frame, wherein the response frame comprises the requested personal training data item.

7. The method of claim 6, further comprising repeating said exchange of the request frame and the response frame for each personal training data item.

8. The method of claim 1, wherein the frame is a write request frame specifying a write command for a personal training data item comprised in the request frame, the method further comprising transferring a response frame associated with the request frame, wherein the response frame is an acknowledgment to indicate that the data writing has been successfully completed.

9. The method of claim 1, wherein one of the first Bluetooth device and the second Bluetooth device is a server device and the other is a client device, wherein the server device stores the personal training data in a permanent manner, and wherein the client device stores the personal training data in a temporary manner.

10. The method of claim 9, wherein the client device discards the personal training data after disconnecting with the server device.

11. The method of claim 9, wherein the server device is a personal training device of a user and the client device is a gym training apparatus.

12. The method of claim 1, wherein dedicated locations are provided for said information elements in a header of the at least one frame, and wherein a unique combination of values of said information elements specifies that the frame belongs to the personal training data service.

13. The method of claim 1, further comprising:
carrying out the service discovery of the personal training data service only when bonding the first Bluetooth device with the second Bluetooth device for the first time;
storing service parameters of at least one discovered service during the service discovery procedure; and
using the stored service parameters in subsequent bondings of the first Bluetooth device with the second Bluetooth device for the first time.

14. The method of claim 1, further comprising providing at least one of the following personal training data item groups, each group comprising at least one personal training data item: user attributes, user's contact information, user's physiological parameters, training configuration parameters, training program parameters, measurement data, and accumulated performance data.

15. An apparatus comprising:
at least one processor; and
at least one tangible computer readable storage medium storing instructions that, when executed by the at least one processor, cause the at least one processor to perform operations comprising:
initiating a Bluetooth connection establishment with a second Bluetooth device;
carrying out a service discovery procedure with the second Bluetooth device, during which the first Bluetooth device informs the second Bluetooth device of a personal training data service and broadcasts a radio frequency discovery frame comprising at least one unique service identifier that uniquely identifies the personal training data service, wherein the personal training data service is provided by the first Bluetooth device and processes at least one personal training data item that represents personal training data associated with a user during a physical exercise;
after the service discovery procedure, transferring at least one radio frequency frame from the second Bluetooth device, wherein the radio frequency frame comprises an information element specifying personal training data associated with a user of the discovered personal training data service and a command information element specifying how to process the personal training data specified by the information element associated with the frame.

16. The apparatus of claim 15, wherein the operations further comprise:
associating each personal training data item with a unique identifier;
exchanging at least one unique identifier of the personal training data during the service discovery procedure so as to determine at least one personal training data item associated with the personal training data service; and
arranging the at least one frame to comprise an information element specifying a personal training data item referred to by the frame.

17. The apparatus of claim 16, wherein the operations further comprise:
associating each unique identifier of the personal training data item with a handle identifier specifying location of the personal training data item in a database of the personal training data service; and
providing the handle identifier in each frame to specify the personal training data item referred to by the frame.

18. The apparatus of claim 17, wherein the operations further comprise exchanging a structure of the database during the service discovery procedure by exchanging said handle identifiers of the personal training data items stored in the database.

19. The apparatus of claim 15, wherein the operations further comprise providing a frame comprising no personal training data item or only one personal training data item.

20. The apparatus of claim 15, wherein the operations further comprise providing dedicated locations for said information elements in a header of the at least one frame, and wherein a unique combination of values of said information elements specifies that the frame belongs to the personal training data service.

21. The method of claim 1, wherein the advertisement frame comprises a name of the first Bluetooth device and a name of an owner of the first Bluetooth device.

* * * * *

UNITED STATES PATENT AND TRADEMARK OFFICE
CERTIFICATE OF CORRECTION

PATENT NO.         : 9,648,108 B2                                   Page 1 of 1
APPLICATION NO.    : 14/440212
DATED              : May 9, 2017
INVENTOR(S)        : Granqvist et al.

It is certified that error appears in the above-identified patent and that said Letters Patent is hereby corrected as shown below:

In the Specification

Column 2, Line 23:
Now reads: "... of may be a ..."
Should read: "... may be a ..."

Column 15, Line 4:
Now reads: "... computer progress executed ..."
Should read: "... computer program executed ..."

Signed and Sealed this
Second Day of January, 2018

Joseph Matal
*Performing the Functions and Duties of the*
*Under Secretary of Commerce for Intellectual Property and*
*Director of the United States Patent and Trademark Office*